(12) United States Patent
Pollack et al.

(10) Patent No.: US 8,254,657 B2
(45) Date of Patent: Aug. 28, 2012

(54) IMAGE RECOGNITION AND ANALYSIS SYSTEM AND SOFTWARE

(75) Inventors: Michael J. Pollack, Lansdale, PA (US); Branson J. Darnell, Harleysville, PA (US); Steven J. Mandrachia, Eagleville, PA (US); Gary Reichl, Coopersburg, PA (US); Richard A. DiDomizio, Hatfield, PA (US)

(73) Assignee: Pollack Laboratories, Inc., Colmar, PA (US)

( * ) Notice: Subject to any disclaimer, the term of this patent is extended or adjusted under 35 U.S.C. 154(b) by 1179 days.

(21) Appl. No.: 11/970,313

(22) Filed: Jan. 7, 2008

(65) Prior Publication Data

US 2008/0166037 A1 Jul. 10, 2008

Related U.S. Application Data

(60) Provisional application No. 60/883,829, filed on Jan. 8, 2007.

(51) Int. Cl.
*G06K 9/00* (2006.01)
(52) U.S. Cl. .......................... 382/133; 382/100; 382/128
(58) Field of Classification Search .................. None
See application file for complete search history.

(56) References Cited

U.S. PATENT DOCUMENTS

| | | | |
|---|---|---|---|
| 3,809,607 A | 5/1974 | Murrey et al. | |
| 4,393,466 A | 7/1983 | Deindoerfer et al. | |
| 4,659,218 A * | 4/1987 | de Lasa et al. | 356/133 |
| 4,814,868 A | 3/1989 | James | |
| 4,893,935 A | 1/1990 | Mandel et al. | |
| 4,965,601 A | 10/1990 | Canty | |
| 4,977,418 A | 12/1990 | Canty | |
| 5,152,175 A * | 10/1992 | Reynolds | 73/19.01 |
| 5,182,791 A | 1/1993 | Pollack | |
| 5,230,556 A | 7/1993 | Canty et al. | |
| 5,425,279 A | 6/1995 | Clark et al. | |
| 5,532,389 A * | 7/1996 | Trent et al. | 549/522 |
| 5,561,520 A | 10/1996 | Williams | |
| 5,956,077 A | 9/1999 | Qureshi et al. | |
| 6,047,082 A * | 4/2000 | Rhody et al. | 382/141 |
| 6,049,381 A | 4/2000 | Reintjes et al. | |
| 6,051,518 A * | 4/2000 | Srivastava et al. | 502/20 |
| 6,111,599 A | 8/2000 | Nance et al. | |
| 6,122,042 A | 9/2000 | Wunderman et al. | |
| 6,134,342 A * | 10/2000 | Doke et al. | 382/141 |
| 6,252,980 B1 * | 6/2001 | Schwartz et al. | 382/141 |
| 6,438,261 B1 * | 8/2002 | Moshe et al. | 382/133 |
| 6,450,655 B1 | 9/2002 | Walck et al. | |

(Continued)

*Primary Examiner* — David A Vanore
*Assistant Examiner* — Andrew Smyth
(74) *Attorney, Agent, or Firm* — Howson & Howson LLP

(57) ABSTRACT

A method of analyzing bubbles, cells, cell viability, or other particles or agglomerates in a process liquid contained in a vessel is provided. Images of bubbles, cells or other particles in the liquid are obtained in-situ with a vision probe extending through a wall of the vessel. The images are analyzed with image recognition software. The software measures at lease one of bubble, cell or particle size, mean diameter, surface area, flow rate, flow pattern, population distribution, viability, agglomerates or clumping, color change, viscosity, Sauter mean, ratio of surface area of bubbles relative to volume of bubbles, gas hold-up ratio of gas volume to volume of liquid, or interfacial area. The software distinguishes valid or viable bubbles, cells or particles that should be included in an analysis from invalid or non-viable bubbles, cells or particles that should not be included. The software can be configured to provide an analysis of the valid bubbles, cells or particles that fall within pre-set size and shape or viability parameters.

12 Claims, 7 Drawing Sheets

U.S. PATENT DOCUMENTS

| | | |
|---|---|---|
| 6,603,117 B2 | 8/2003 | Corrado et al. |
| 6,629,449 B1 | 10/2003 | Kline-Schoder et al. |
| 6,660,995 B1 | 12/2003 | Canpolat et al. |
| 6,673,532 B2 | 1/2004 | Rao |
| 6,723,981 B2 | 4/2004 | Corrado et al. |
| 6,782,184 B2 | 8/2004 | Canty et al. |
| 6,806,900 B2 | 10/2004 | Eversole et al. |
| 6,849,308 B1* | 2/2005 | Speakman et al. ............ 427/595 |
| 6,873,725 B2 | 3/2005 | Xu |
| 6,888,631 B2 | 5/2005 | Eriksson |
| 6,960,756 B1 | 11/2005 | Penumadu et al. |
| 7,041,493 B2 | 5/2006 | Rao |
| 2002/0101508 A1* | 8/2002 | Pollack ......................... 348/85 |
| 2004/0036859 A1* | 2/2004 | Silverman et al. ......... 356/237.1 |
| 2004/0037813 A1 | 2/2004 | Simpson et al. |
| 2004/0095577 A1 | 5/2004 | Eckardt et al. |
| 2005/0046841 A1 | 3/2005 | Rabinski et al. |
| 2005/0134845 A1 | 6/2005 | Bordelon |
| 2005/0199818 A1* | 9/2005 | Tomita et al. ............ 250/370.01 |
| 2005/0244863 A1 | 11/2005 | Mir |
| 2006/0017930 A1 | 1/2006 | Canty et al. |
| 2006/0029946 A1 | 2/2006 | Hahn |
| 2006/0152730 A1 | 7/2006 | Schneider |
| 2006/0256340 A1 | 11/2006 | Hansen et al. |
| 2006/0257999 A1 | 11/2006 | Chang et al. |
| 2007/0155985 A1* | 7/2007 | Wonders et al. .............. 562/410 |
| 2007/0155986 A1* | 7/2007 | Wonders et al. .............. 562/410 |
| 2007/0208194 A1* | 9/2007 | Woodruff et al. ............. 562/410 |
| 2008/0143828 A1 | 6/2008 | Mandrachia et al. |

* cited by examiner

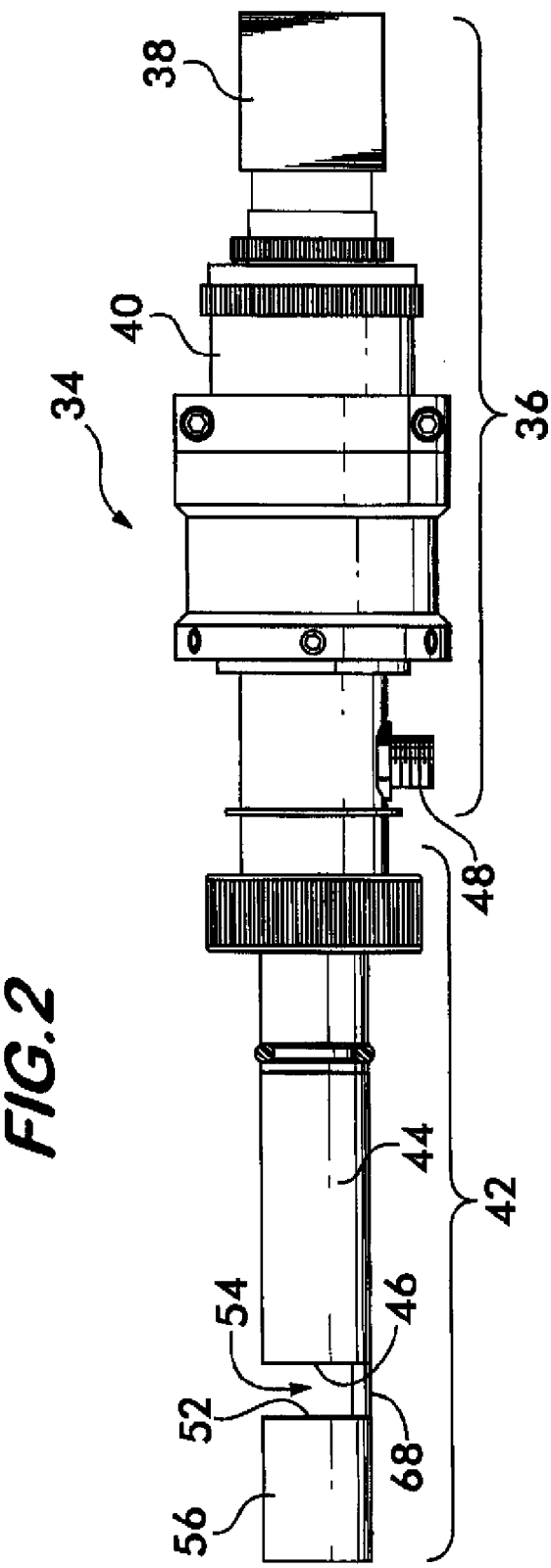

FIG. 8
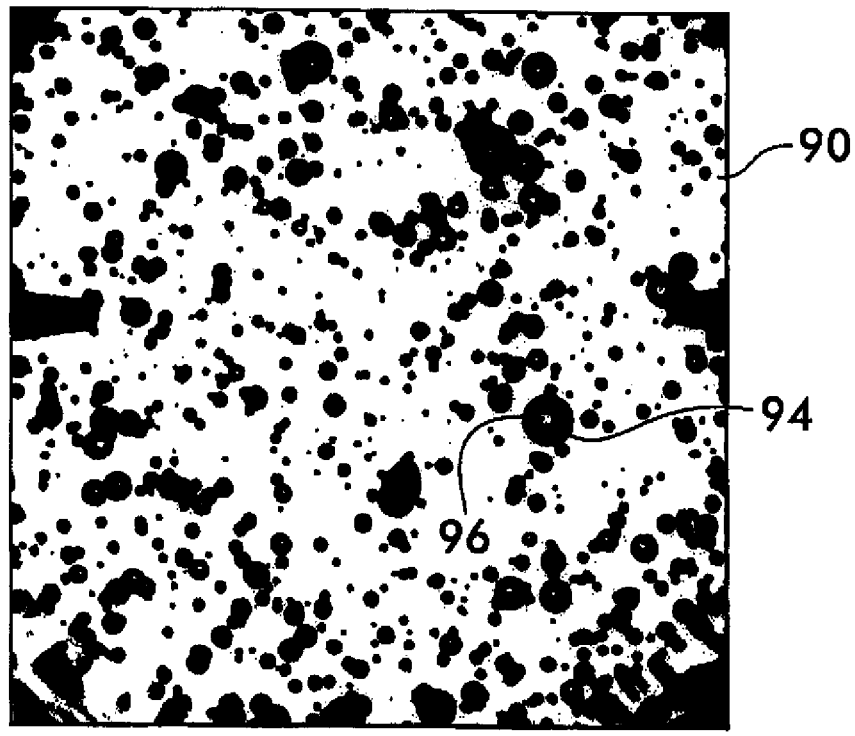
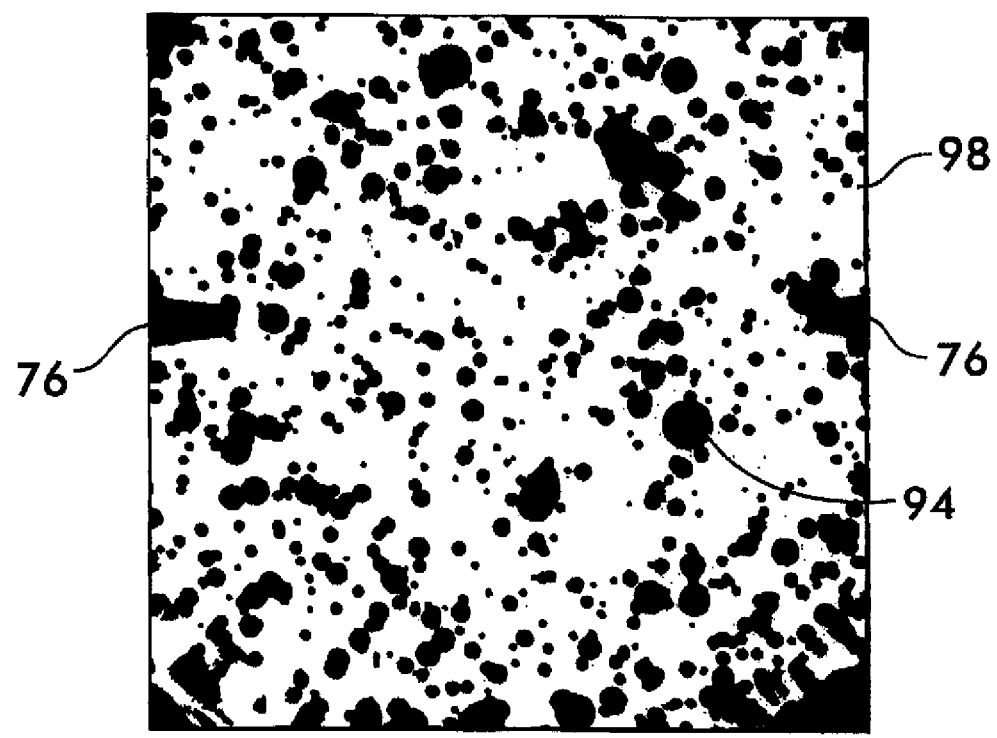
FIG. 9

FIG.12
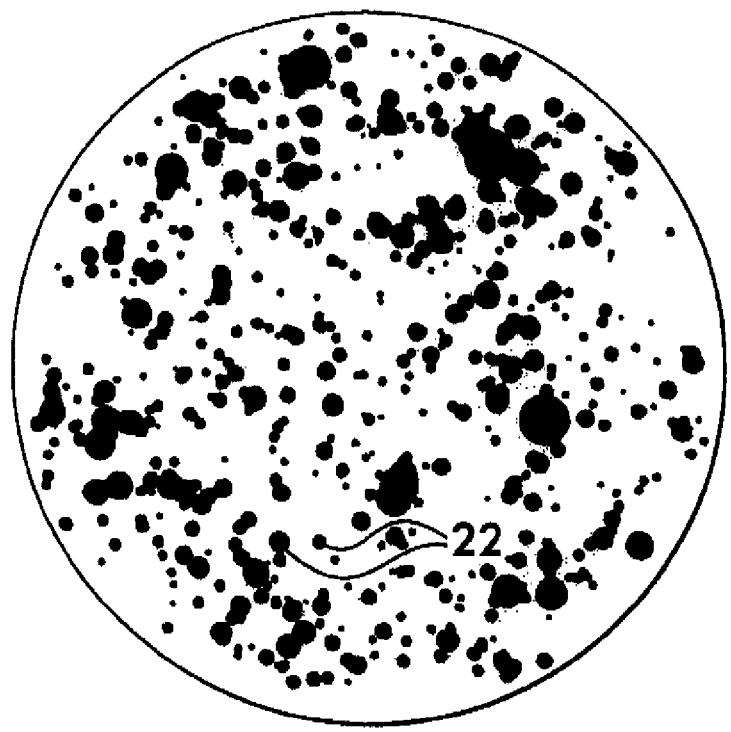
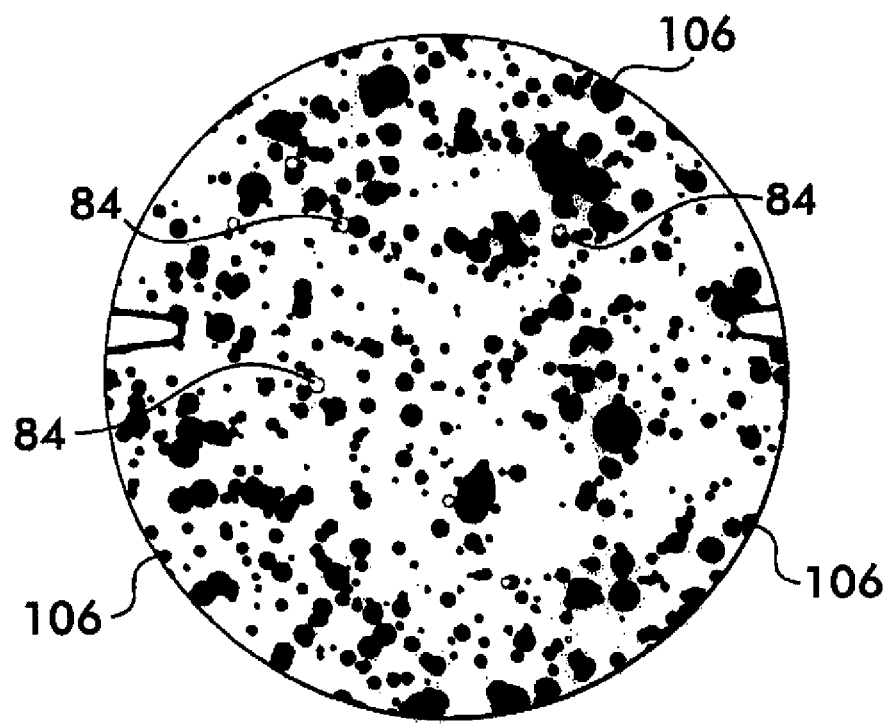
FIG.13

IMAGE RECOGNITION AND ANALYSIS SYSTEM AND SOFTWARE

CROSS-REFERENCE TO RELATED APPLICATION

This application claims the benefit under 35 USC §119(e) of U.S. Provisional Patent Application No. 60/883,829, filed Jan. 8, 2007.

BACKGROUND OF THE INVENTION

The present invention relates to image recognition computer software and the use thereof to analyze images of bubbles or particles, and more particularly, the present invention relates to a system of observing and analyzing a process occurring within a vessel.

The production of biopharmaceuticals, enzymes and other biotechnology derived compounds typically takes place in a vessel, such as a bioreactor, fermenter, or the like. As an example, a vessel may include a sparger for introducing a gas, such as compressed air, directly within the liquid in the form of bubbles. The bubbles are typically required to be of an appropriate size and volume and to be injected at an appropriate rate into the process liquid so that the gas is absorbed uniformly throughout the process liquid before reaching the surface of the liquid. Such a vessel also typically includes an agitator provided as one or more rotating blades.

Problems often arise with respect to the injection of gas into a process liquid. For example, if the size, volume, quantity, or injection rate of bubbles and/or parameters, such as bubble size versus volume, is too great, a significant quantity of the bubbles reach the surface of the process liquid without being absorbed and creates an undesirable amount of foam in the headspace of the vessel. The presence of too much foam can effectively close off the upper surface of the process liquid, thereby starving the culture of oxygen, and/or can clog filters. Problems can also occur if the size, volume, quantity, or injection rate of bubbles and/or parameters, such as bubble size versus volume, is too small. In this case, only localized areas of the process liquid is sufficiently aerated and an overall sufficient amount of absorption and uniform absorption fail to occur.

Problems are also presented by the agitator. The agitator can function to shear the bubbles to smaller sizes and to distribute gas bubbles by creating turbulence. An agitator can also create partial vacuums within the process liquid and generate air bubbles via cavitation thereby pulling air into the process liquid from the headspace. If the blades of the agitator rotate too swiftly, bubbles of an undesirable large size may be generated, too much turbulence may be generated, and too much foam may be caused to form in the headspace. Thus, an appropriate amount of agitation must be utilized to accomplish specific objectives of a given process and to strike a desired balance between aeration as a result of the output of the sparger versus aeration as a result of cavitation.

Adjustments to the quantity, volume, bubble size, bubble size versus volume, and rate of gas introduced into a process liquid and to the speed of rotation of the agitator within a vessel are typically made based on past experiences, objective parameters, and yields, and not by direct observation or analysis.

Further, changes in viscosity of the process liquid typically occur during a process. For example, cell culture growth during a process will change the viscosity of the process liquid. In some cases the process liquid changes from a water-like viscosity to a more dense syrup-like viscosity. This changes the flight, absorption, size and other characteristics of the bubbles within the process liquid. Thus, monitoring these changes and providing real-time adjustments could greatly improve such processes and/or could be used to prevent excess foam formation or clogging of filters.

Accordingly, there is a need for a system and method utilizing image recognition software that enables real time in-situ observation and analysis of processes being performed in process vessels.

BRIEF SUMMARY OF THE INVENTION

The present invention relates to image recognition software for analyzing images of a process liquid during a production process or testing procedure within a vessel. The information generated by the software can include, for example, the quantity and volume of bubbles, cells or particles in the images, the size of the bubbles, cells or particles, the size of the bubbles, cells or particles versus volume, the mean diameter of the bubbles or particles, the surface area of the bubbles or particles, the flow rate of the bubbles, cells or particles, the flow pattern of the bubbles, cells or particles, the population distribution of the bubbles, cells or particles, cell viability, the presence of agglomerates or clumping, the color change of cells or particles, temperature and viscosity of the process liquid, Sauter mean, gas mass transport, the ratio of surface area of bubbles relative to volume of bubbles, gas hold-up ratio of gas volume to volume of liquid, and interfacial area (i.e., amount of surface area of bubbles in direct contact with liquid). This information can be used as a control tool to implement changes to process operating parameters in real time.

According to one contemplated embodiment of the present invention, the software analyzes images taken by a vision probe extending into a vessel. Preferably, the probe has a camera for recording still or motion images of the process liquid and gas bubbles, cells, or other particles. The probe has a distal end that extends within an interior of the vessel and that is housed within a hermetically sealed protective shroud. The distal end has a one or a plurality of lenses, or windows, through which images are recorded by the camera and carries a means for projecting light within the vessel so that images recorded by the camera are front lit, back lit, or both. The camera transfers information of the recorded images to a computer or like processor on which the image recognition software is loaded.

A contemplated use of the present invention is in connection with a process vessel having a sparger and an agitator. The sparger releases gas in the form of bubbles directly into the process liquid, and the agitator distributes and shears the bubbles and may generate additional bubbles via cavitation. The software analyzes bubble characteristics so that adjustments can be made to the process, such as adjustments to the operation of the sparger and agitator, in real time to achieve a desired result.

According to a further aspect of the present invention, a method of analyzing bubbles or particles in a process liquid contained in a vessel is provided. Gas in the form of bubbles is released from a sparger in the process liquid within the vessel and the gas bubbles are sheared and distributed within the process liquid via an agitator. The gas bubbles are observed in-situ with a probe extending within the vessel. Observation of the process liquid and bubbles includes projecting light from the probe into the vessel to illuminate the gas bubbles and recording images of the illuminated bubbles with a camera mounted on the probe. The images are analyzed, preferably in real time, with image recognition and analysis software. For instance, the software measures bubble size, mean diameter, surface area, flow rate, flow pattern, population distribution, cell viability, agglomerates or clumping, color change, temperature, viscosity, Sauter mean, gas mass transport, the ratio of surface area of bubbles relative to volume of bubbles, gas hold-up ratio of gas volume to volume of liquid, and interfacial area. Such information can be used to control a process condition in the sealed vessel.

These visual observations can also be compared and used with like observations obtained from other areas within the same process and vessel or from observations from other processes and vessels. For example, the differences in the results provided by changing a process parameter can be readily determined from such a comparison and analytical results of future processes can therefore be better anticipated. Accordingly, the use of the vision probes and software not only yield additional information about an on-going process but also can be to demonstrate the interaction between various analytical methodologies.

BRIEF DESCRIPTION OF THE DRAWINGS

The foregoing and other objects, features and advantages of the present invention should become apparent from the following description when taken in conjunction with the accompanying drawings, in which:

FIG. 2 is a side elevational view of a vision probe according to the present invention;

FIG. 8 is a view representing the binary image of FIG. 7 with speckles of one or two pixels removed;

FIG. 9 is a view representing the binary image of FIG. 8 with the white centers of annular bubbles shown in black;

FIG. 12 is a view representing the binary image of FIG. 9 minus the binary image of FIG. 11; and FIG. 13 is a view of the binary image of FIG. 9 minus the binary images of FIGS. 5 and 10.

DETAILED DESCRIPTION OF THE INVENTION

The present invention relates to a system and method for analyzing bubbles, cells, or other small particles in a process liquid. For example, gas released from a sparger within a process liquid contained in a vessel may be observed in-situ with at least one vision probe extending through one or more access ports in the walls of the vessel. The gas bubbles within the process liquid may be distributed and sheared within the liquid by an agitator located adjacent the sparger. The vessel may have multiple access ports located at different locations for enabling different areas within the vessel to be observed. The vision probes are mounted within the access ports and may include interchangeable parts, such as cameras, lens assemblies, sensors, light guides, light sources, etc., permitting a desired observation to be obtained.

The bubbles, cells, or other particles are observed by projecting light from the vision probe into the vessel to illuminate the gas bubbles, cells, or other particles and by recording images of the illuminated bubbles, cells, or other particles with a camera mounted on a proximal end of the probe. In most instances, the camera is located on an ambient side of the vessel wall and may be periodically moved from one probe to the next allowing observations to be made at different locations within the vessel without disrupting an ongoing process in the vessel. If backlit or silhouette images of the bubbles or particles are desired, the probe is provided with a distal end that emits or reflects light from behind the gas bubbles or particles toward the direction of the camera. Alternatively, the distal end can be designed to project light forward of the distal end so that front lit images can be obtained. In some cases, the camera may be located within a sealed protective canister within the vessel.

The recorded images are transferred to a computer processor or the like having image recognition and analysis software. The software analyzes the images and determines information therefrom concerning the ongoing process or the mechanical operation or cleanliness of the vessel. For example, the software may obtain measurements of bubble, cell or other particle size, mean diameter, surface area, flow rate, flow pattern, and population distribution, as well as cell viability, agglomerates or clumping, color change, temperature, viscosity, Sauter mean, gas mass transport, the ratio of surface area of bubbles relative to volume of bubbles, gas hold-up ratio of gas volume to volume of liquid, interfacial area or the like. This information can be provided in substantially real time so that corrective adjustments can be made to an ongoing process within the vessel. Accordingly, the observation, analysis and measurements provided by the vision analysis system enables problems to be anticipated and preventive actions to be taken to adjust the parameters of an on-going process to maximize the effectiveness of the process.

Vessel and Probe Apparatus

Figure 1:
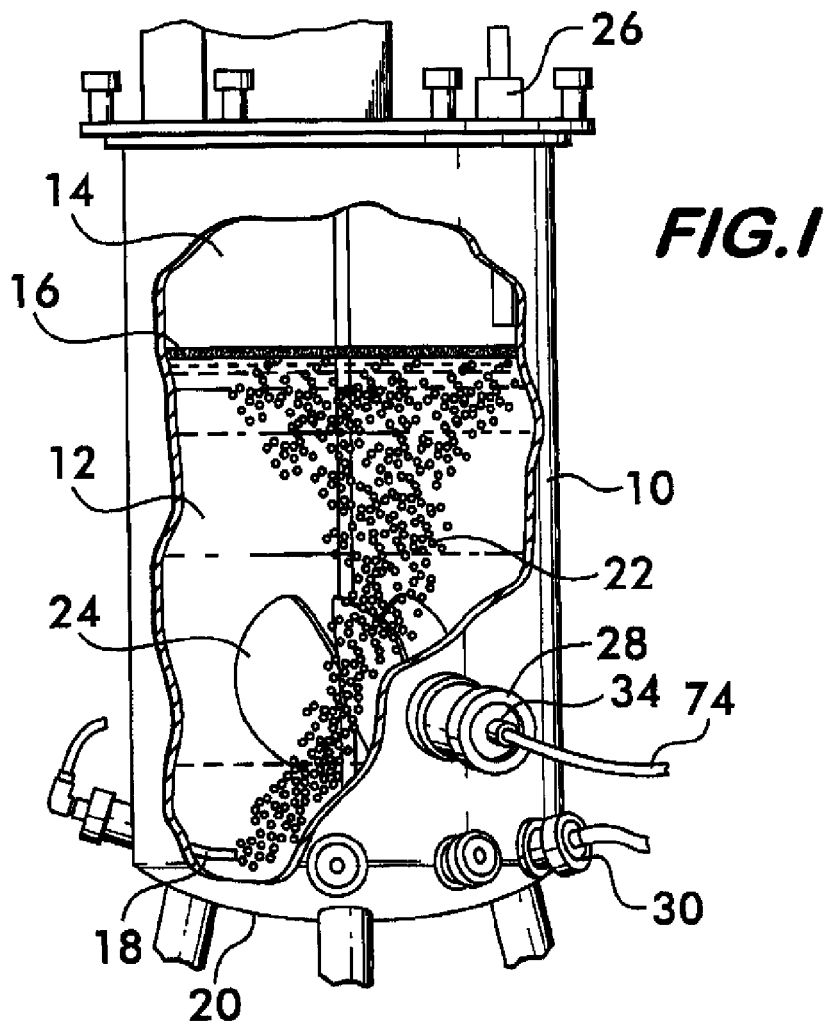
FIG. 1 is a partially-cutaway front elevational view of a sealed vessel having a vision analysis system according to the present invention.
Figure 3:
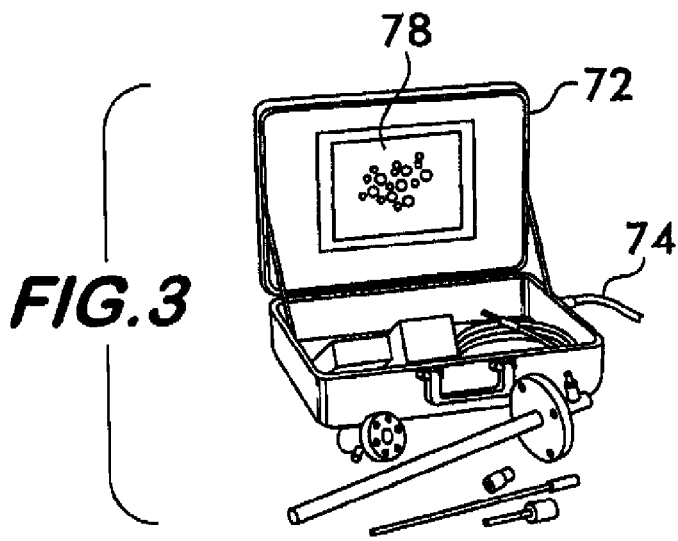
FIG. 3 is a perspective view of a portable, modular vision analysis system according to the present invention.

An example of a process vessel, tank, vat, or pipe 10 according to the present invention is illustrated in FIG. 1. The vessel 10 can be a sealed vessel that is closed at its upper and lower ends, or an unsealed vessel that has an open upper end. For purposes of example, the vessel 10 can be a bioreactor or microbial fermenter used in the production of biopharmaceuticals, enzymes or other biotechnology derived compounds. The vessel according to the present invention is not limited to bioreactors and fermenters nor is it limited to the production of the above referenced substances. The present invention is directed to any type of sealed or unsealed vessel or pipeline in which a process, such as fermentation or the like, is being performed therein.

The illustrated vessel 10 contains a process liquid 12 and defines a headspace 14 located above a surface 16 of the liquid 12. A sparger 18 is located near the base 20 of the vessel 10 and injects a gas, such as compressed air, into the liquid 12. At least a majority of the gas bubbles 22 are intended to be absorbed by the liquid 12 before being able to float to the upper surface 16 of the liquid 12. An agitator 24, such as rotating blades, is located above the sparger 18 to distribute and shear the bubbles 22. The agitator 24 can also be utilized to generate additional bubbles via cavitation, if desired. As an alternative to gas bubbles, other substances, particles or the like can be infused into the process liquid.

The vessel 10 illustrated in FIG. 1 has three access ports, 26, 28 and 30. The access port 28 permits observation of the mechanical motion of the agitator, or impeller, 24, the cleanliness of the agitator 24, as well as various characteristics of the bubbles 22 adjacent the agitator 24 (ie., distribution, reduction, flow rate, flow pattern, etc.). Bioreaction yield is affected by the distribution of bubbles through the liquid. In cell culture, primary agitators are typically axial flow type agitators, and in microbial fermentation, agitators are typically radial flow type agitators. Observation in real time through access port 28 enables problems with respect to gas flooding or cell clumping to be recognized so that corrective adjustments can be made during the process. Accordingly, the observations provided by the present invention permit the present invention to be an analytical tool as well as a process control tool The access port 30 permits observation of the operation of the sparger 18 and the characteristics of the bubbles 22 emanating therefrom (ie., size, population, rate, etc.). Cell growth and product expression depend heavily on gas mass transfer. In cell culture, it is useful to know bubble size, gas volume, bubble size as a percent of gas volume, number of bubbles, and rate as a function of gas flow rate through the sparger. Cell viability, the presence of agglomerates or clumping, color change, temperature, viscosity, Sauter mean, gas mass transport, the ratio of surface area of bubbles relative to volume of bubbles, gas hold-up ratio of gas volume to volume of liquid, and interfacial area may also be important to determine. In microbial fermentation, it is important to know the bubble size, bubble size as a percent of gas volume, number and rate as function of both gas flow rate and the RPM of the high-shear impeller blades.

A vision probe 34 is mounted in at least one of the access ports 28 and 30. A proximal end 36 of the probe includes a camera 38 and an optical lens assembly 40. When the vision probe is mounted to the vessel 10 via one of the access ports, 28 and 30, the proximal end including the camera 38 and lens assembly 40 is located on the ambient, or external, side of the wall of the vessel 10. This enables the camera and lens assembly to remain functional despite the hostile environment and temperatures within the vessel. Preferably, the probe 34 is gas cooled and/or heated to further protect the camera and lens assembly as well as other probe components from processes performed at high and/or low temperatures. As an example, temperatures may reach up to 600° C. within the vessel, and cool gas may be pumped and circulated deep within the probe 34 so that the probe 34 remains operational. As an alternative, the probe 34 can be liquid cooled and/or heated.

The camera 38 can be any device capable of taking or recording still or motion images in any format, and the lens assembly 40 can be provided and adjusted as desired to obtain a desired image. As an example, the camera 38 can record black and white or color images, still images or video images, or can be an infrared camera.

The probe 34 includes a distal end 42 interconnected to the proximal end 36. When the probe 34 is mounted to the wall of the vessel 10, the distal end 42 extends through one of the ports, 28 and 30, so that it is located and extends directly within the liquid 12 in the vessel 10. The distal end 42 is hermetically sealed within a protective shroud 44. Thus, the outside of the shroud 44 can be immersed within the process liquid in the vessel and prevents the process liquid from entering into the probe 34. Accordingly, the shroud 44 is capable of tolerating the hostile environment within the vessel 10 so that it can protect the other components of the probe 34 from damage. During a process, the shroud 44 remains in place within one of the ports, 28 and 30, and permits other components of the probe 34 to be removed, replaced and/or re-installed without disturbing the process occurring within the vessel 10.

The shroud 44 can be rigid or flexible. For example, the shroud can be a rigid tube of stainless steel, titanium, or other compliant material. Alternatively, the shroud can have flexible bellows, joints, telescopic sections or the like so that the probe can be articulated or robotically moved to, or pointed at, an area of interest within the vessel during an on-going process. The controls for moving or manipulating the probe can be located external of the vessel. A moveable, flexible probe enables information with respect to a reaction taking place at a particular location within the vessel to be obtained. It can also be used to aim the tip of the probe at a desired angle within the vessel so that the flow of bubbles can be viewed in a desired manner. For instance, an angle or location may be selected that makes it less likely for bubbles or particles to stick to the window of the probe.

A high pressure lens, or window, 46 is secured to and seals an opening in the shroud 44 through which images are recorded by the camera 38. As an example, the lens 46 can be a high purity annealed sapphire window. Alternatively, it can be made of ruby or a synthetic material such as polycarbonate. The window 46 can include calibration markings 76 to aid in the determination of the size of the bubbles or particles shown in the recorded images. Preferably, a transmission media extends longitudinally within the shroud 44 and provides an optical path for the camera 38 from the optical lens assembly 40 to the window 46. An example of a transmission media is a coherent fiber optic bundle that transmits images in a coherent manner from one end to the other.

The probe 34 also includes means for directing light from the distal end 42 into the vessel 10. For example, a light source of light emitting diodes (LEDs) can be provided directly within the probe 34, such as adjacent to the window 46 in the distal end 42 of the probe. An advantage of the use of LEDs is that they can produce light waves within a wide frequency range. For example, LEDs can produce near infrared (IR) light. Such so-called "red light" enables better image resolution in various solutions such as opaque liquids. LEDs that emit ultraviolet (UV) light are also useful since they can provide better penetration. In addition, UV light is also useful for cleaning validation, particularly when the vessel is treated with organic compounds that glow when illuminated with UV light.

Alternatively, a light source can be located externally of the probe 34. In this case, a light guide can extend longitudinally within the distal end 42 from a light source connector 48 to the window 46. The external light source can be connected to the probe 34 via a fiber optic line. Examples of light guides include fiber optic light guides, liquid light guides, and acrylic light guides.

The distal ends of the probes of the present invention can be provided in different types and can be interchangeable. For example, the distal end 42 of probe 34 is designed to provide back lit images so that bubbles or like particles are silhouetted against light directed toward the camera 38. In the illustrated embodiment, a backscreen 52 is spaced from and faces the window 46 to provide light directed and focused only toward the camera. An opening, or gap, 54 extends transversely through the distal end 42 such that liquid 12 and bubbles 22 can flow directly between the window 46 and the backscreen 52. The backscreen 52 emits or reflects light thereby enabling the camera 38 to record back lit images of the bubbles.

Illumination of the backscreen 52 can be provided by a light source contained in the backscreen extension 56 or by a light guide extending into the extension 56 via the bridge connection 68. Alternatively, the backscreen 52 can be formed of a reflective material, such as a mirror or ceramic plate, and reflect light being emitted in a forward direction from window 46 back toward the camera 38. Preferably, the backscreen 52 is a directional light source that emits light focused only toward the camera and does not emit light in all directions within the vessel. The directional light source eliminates the possibility of light reflecting off the walls of the vessel or the like from obscuring or reducing the quality of the images obtained by the camera.

Alternate distal ends can be used for recording front lit images, such as images of the headspace and the operation or cleanliness of the agitator, sparger, or interior walls or surfaces of the vessel. Such a tip, for instance, can extend angularly from the distal end to alter the viewing angle or change the view provided to the camera by the lens. The tip can utilize a prism or other types of lens to adjust the viewing angle or provide a desired view. As an example, instead of a straight optical view path through the distal end, the angular tip can alter the path by 5° to 20° or more relative to the longitudinal axis extending through the distal end. A tip positioned at a particular angle and location relative to a flow of bubbles within the process liquid may reduce the likelihood of bubbles sticking to the window of the probe. For instance, a probe tip directed substantially parallel to the flow of gas bubbles may tend to minimize bubbles sticking to the window of the probe.

The vision probes can also carry sensors, such as in the distal end of the probe. The sensors can include temperature sensors, pressure sensors, oxygen sensors, spectrographic chemical analysis sensors, and the like. The sensors can be non-contact, optical, point-and-shoot type sensors that take readings at a focal point of the sensors. Thus, the sensors do not necessarily need to be in direct contact with the process fluid. This enables the sensors to be moved from one probe to another during a process without disturbing the process. In addition, the sensors can be interchangeable so that the user can determine which sensor or sensors are required for a particular process or procedure.

The probe 34 can include a fail safe or thermocouple switch that automatically cuts off power to the probe's light source. For example, light sources generate heat and a process on-going within the vessel may be sensitive to temperature. Accordingly, if too much heat is being generated by the light source, the switch automatically cuts off the light source so as not to affect the process. Typically, processes within fermenters may last several days or weeks. Since images may only need to be obtained once every 30 to 60 minutes, the switch can also control the intervals at which the camera and light source are powered. For example, the switch can power the light source for about 5 seconds every 30 to 60 minutes so that the camera can obtain the desired images. In this manner, the heat generated by the light source will be negligible and a temperature sensitive process can be performed in the vessel.

The camera 38 is interconnected to a computer processor 72 or the like to view and/or analyze the recorded images in substantially real time. For example, a computer cable 74 or the like can extend from the camera for the automatic transfer of image data from the camera 38 to the computer processor 72. Alternatively, the camera 38 can store images on a storage device (not shown) which can be manually withdrawn from the camera and input into a computer. Yet another alternative is for the image data to be transmitted from the camera 38 via a wireless connection to the computer processor 72. Information from the sensors can also be automatically fed to the computer processor 72 for analysis, verification, and/or recording. Such information can be used to automatically adjust process parameters of the process occurring within the sealed vessel. Accordingly, the vision system of the present invention can provide remote observation, analysis, verification and historical recording of data of the process occurring within the hostile environment in the vessel and the physical changes occurring therein. Such observations can include observations concerning agitation, aeration, aggregation, foaming, and cleaning.

Image Recognition Software

The computer processor 72 according to the present invention includes image recognition and analysis software. The software is used, for instance, to provide element and constituent analysis and measurements of bubble or particle size, mean diameter, surface area, volume, flow rate, flow pattern, population, distribution, rate of reduction, and color. The analysis provided by the software can be used to adjust process parameters of an on-going process within the vessel 10. As examples, the gas flow rate through the sparger 18 and/or the RPMs of the agitator 24 can be adjusted.

The software provides two major functions. First, the software ascertains which bubbles or particles appearing in the images are so-called "valid" bubbles/particles on which measurements and other data should be collected. For example, bubbles that stick to the surface of the probe window are not valid bubbles and generate errors, if included in measurements. Thus, the software distinguishes "valid" bubbles/particles appearing in the images from "invalid" (ie., cling-on) bubbles/particles. Secondly, the software determines which of the valid bubbles/particles appearing in the images are of a desired size and/or shape for purposes of generating data, such as bubble/particle size, diameter, surface area, volume, flow rate, flow pattern, population distribution, bubble size versus volume, and like characteristics. For example, if only substantially round gas bubbles are of interest, the software determines characteristics of only the round bubbles appearing in the images and eliminates any non-round appearing bubbles from the calculations. Of course, this aspect of the software can be adjusted by the user to obtain the desired data depending on the particular bubbles/particles of interest.

Figure 4:
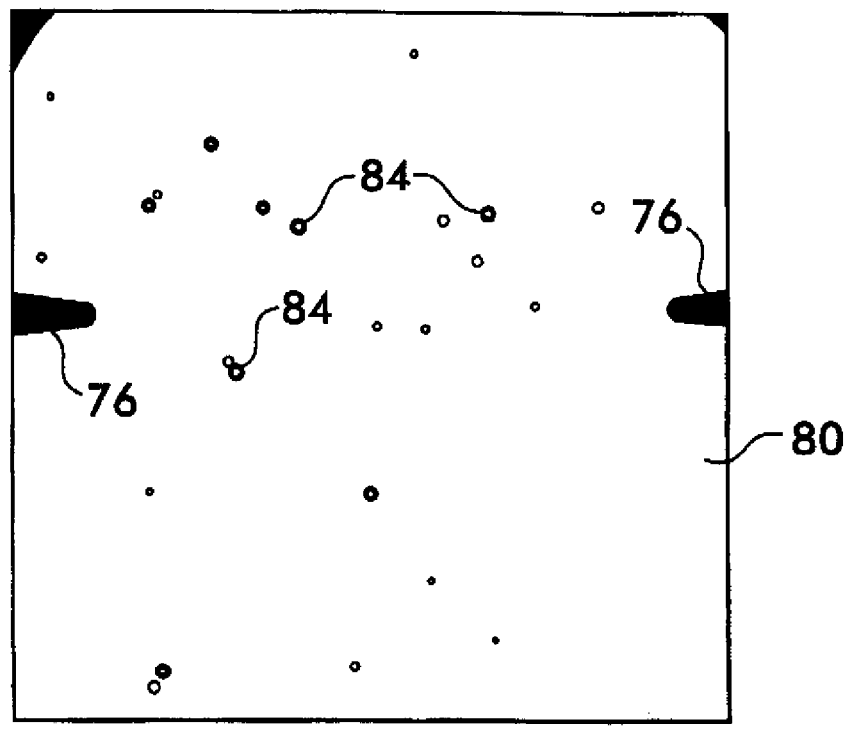
FIG. 4 is a view representing an equivalent image produced as an average of a number of actual images of bubbles taken by vision system of the present application.
Figure 5:
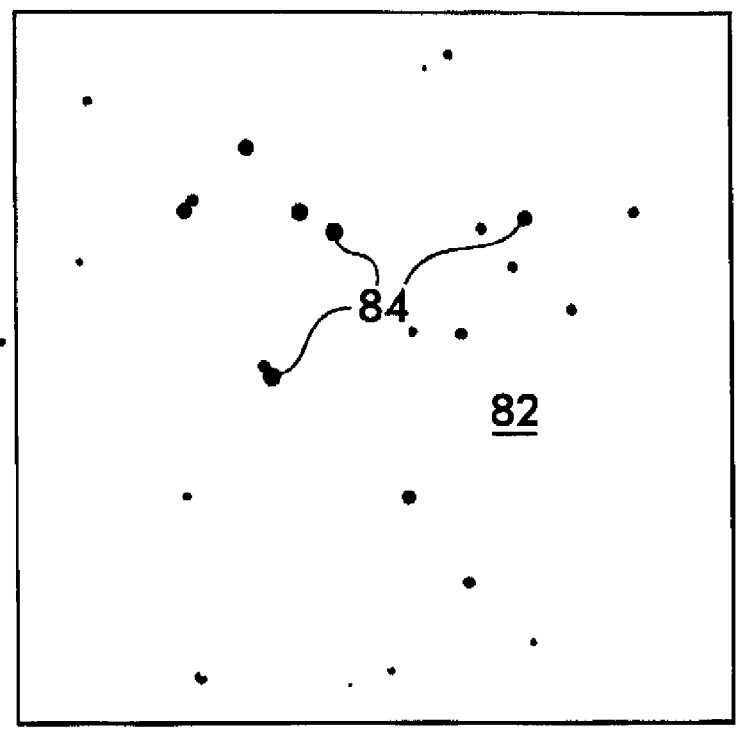
FIG. 5 is a view representing a binary image of FIG. 4.

By way of example, and not by way of limitation, the camera 38 of the probe 34 of the present invention obtains numerous images of bubbles or particles during a pre-determined time period. As an example, the camera 30 may obtain about one hundred consecutive frames of images of the bubbles/particles 22 in the process liquid 12. The software generates an equivalent image 80 from these frames as a result of averaging together the images of all the frames. An example of an equivalent image 80 is illustrated in FIG. 4. The equivalent image 80 identifies the bubbles/particles 84 that repeatedly appear throughout all or a majority of the images. These bubbles/particles 84 are considered "invalid" since they are believed to be stuck to the window 46 of the probe 34 and are not actually flowing in the process liquid 12. A binary image 82 of the equivalent image 80 is illustrated in FIG. 5. The pixels 84 that are represented in black are believed to be "invalid" areas of the images, and the corresponding areas on all of the one hundred frames are not considered in any data collection operation performed by the software on the corresponding frames.

Figure 6:
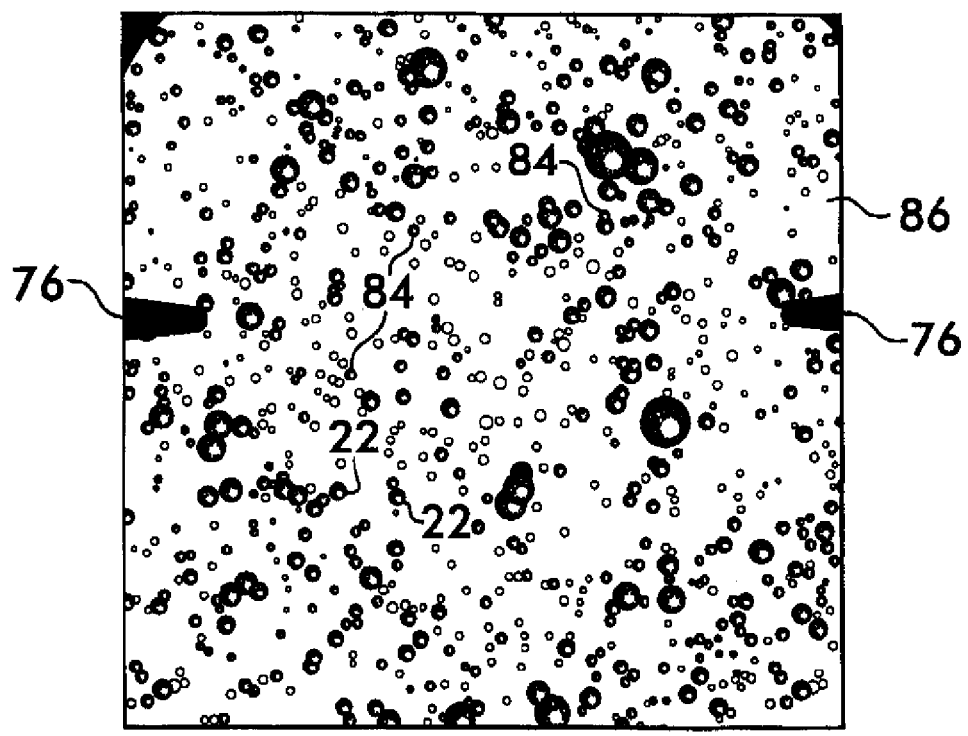
FIG. 6 is a view representing an image of bubbles taken by the vision system of the present application.
Figure 7:
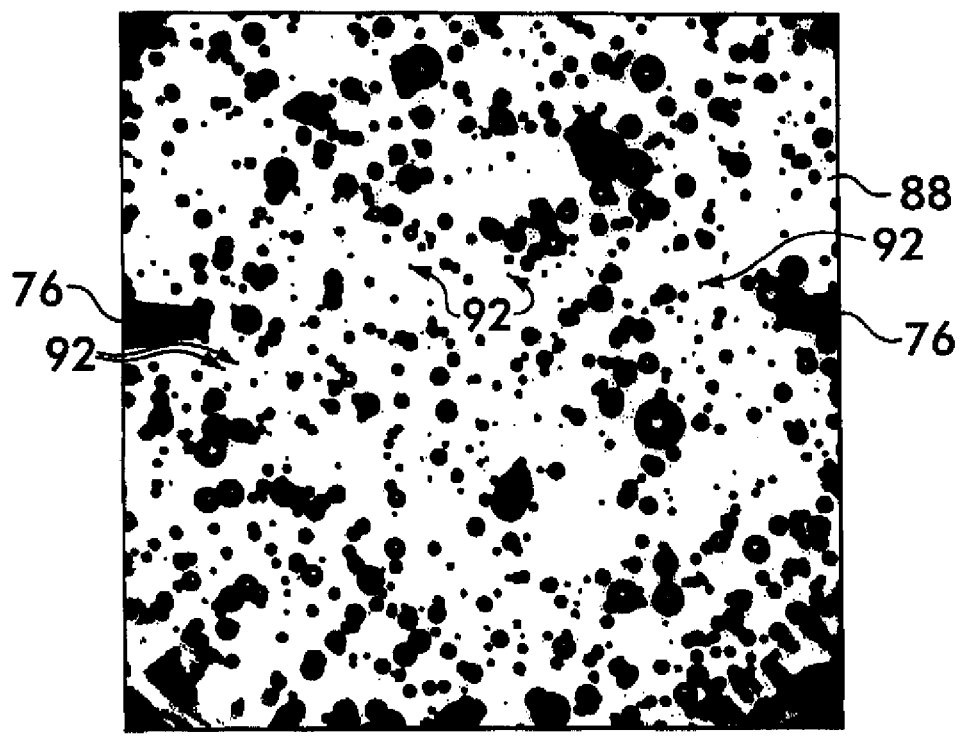
FIG. 7 is a view representing a binary image of FIG. 6.

FIG. 6 is a view of one frame 86 of the above referenced images that was averaged with the other frames to generate the equivalent image 80 illustrated in FIG. 4. Thus, this frame 86 includes "valid" bubbles/particles flowing past the probe 34 in the process liquid 12 as well as the "invalid" bubbles/particles 84 discussed above that are stuck to the probe window 46. A binary image 88 of this single frame 86 is illustrated in FIG. 7.

The software performs a de-speckling operation on the frame 86. Spots appearing in the binary image 88 that are of a size less than a pre-set number of pixels are eliminated. For example, the software can be set to eliminate spots of a size of only one or two pixels from the binary image 88. A de-speckled binary image 90 is illustrated in FIG. 8. As an example, the speckles 92 identified in FIG. 7 have been removed from the de-speckled binary image 90 illustrated in FIG. 8.

When images of gas bubbles are analyzed, many bubbles appear annular with a clear center. Thus, in the binary images, many of the bubbles (shown in black) have white centers. Accordingly, the software determines which pixels in the binary image relate to the center of valid bubbles and changes these pixels to represent a bubble (ie., changes the pixels from white to black). As an example, compare the bubble 94 having a white center 96 in FIG. 8 to the same bubble 94 appearing in the binary image 98 illustrated in FIG. 9.

Figure 10:
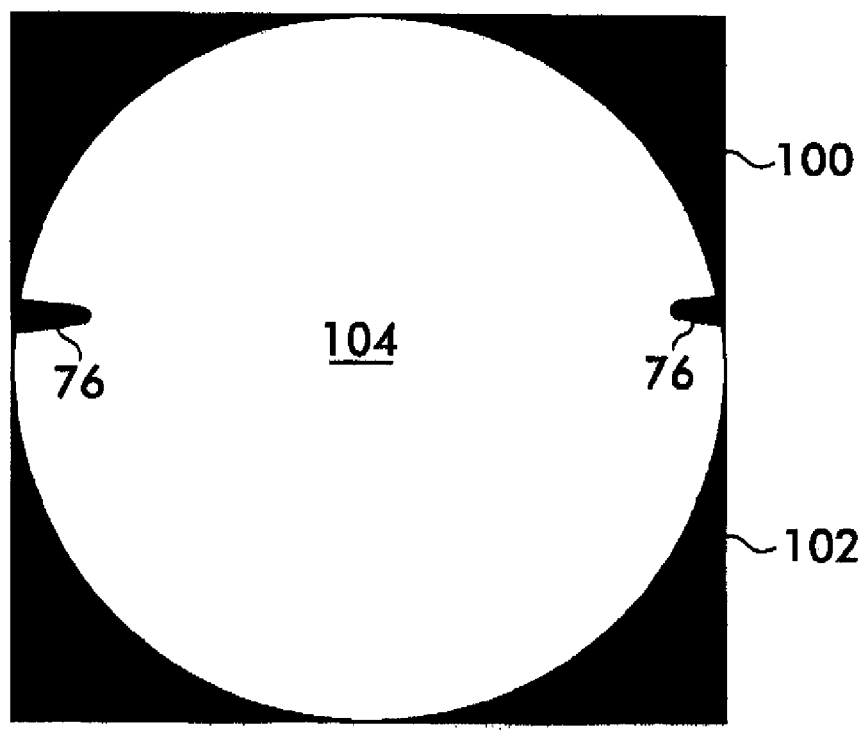
FIG. 10 is a view representing a binary image of the border of the images.

In addition, the software eliminates any bubbles or particles that only partially appear in the images. For example, any bubbles or particles contacting the border of an image is eliminated from consideration. FIG. 10 illustrates a binary image 100 of a border 102 of the images. The white area 104 of FIG. 10 identifies a valid region for bubbles/particles in the images. From this information, the software cancels out any bubbles or particles that appear to contact the border 102 in the images. For example, FIG. 11 shows the bubbles/particles 106 in FIG. 9 that contact the border 102 of FIG. 10.

Figure 11:
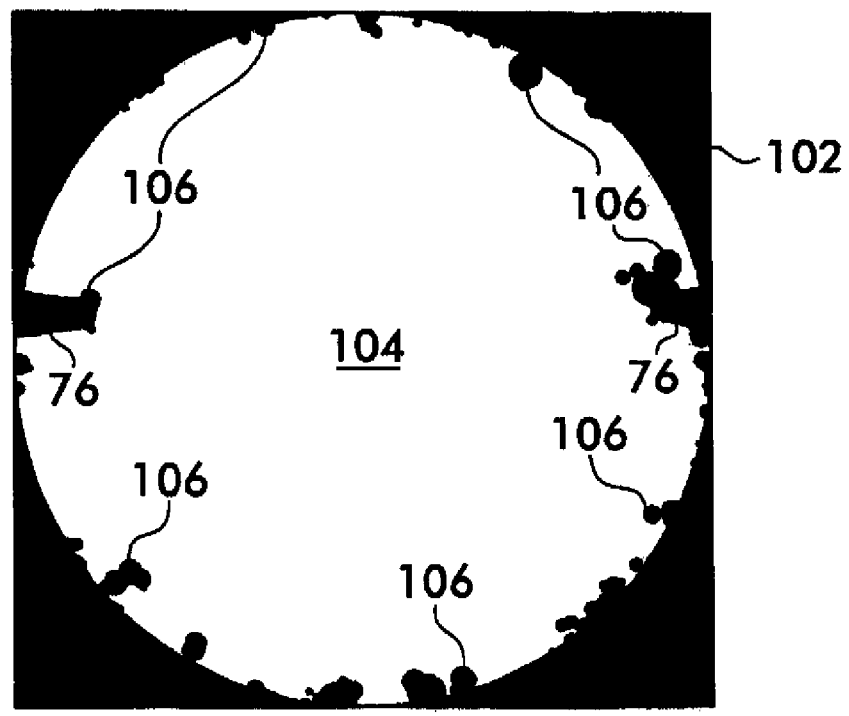
FIG. 11 is a view representing the binary image of FIG. 10 shown with spots in FIG. 9 that contact the border.

The border 102 and bubbles/particles 106 contacting the border 102 shown in FIG. 11 is subtracted from the binary image illustrated in FIG. 9. The result is shown in FIG. 12. Further, the invalid (ie., cling-on) bubbles/particles 84 identified FIG. 5 is subtracted from FIG. 9 and shown in FIG. 13. The software compares and evaluates all spots of FIGS. 12 and 13 that do not contact the invalid (ie., cling-on) bubbles/particles 84 and border 102 and generates a data set for all remaining valid bubbles/particles. The data set includes location within the image, size, shape, area, and the like characteristics determined from the image by the software.

From the above referenced data, the software generates various information based on parameters entered by the user. For example, if bubbles appearing in the images as single, substantially round bubbles of less than a given size are of interest, the software filters the data set to provide only the information requested.

By way of example, the software analyzes each separate spot appearing in a binary image and determines whether the spot is made of one or more circles. If the software determines that a spot comprises a single circle, the software checks the roundness of the circle as well as the area of the circle. If these measurements are within selected pre-set ranges, the data concerning this bubble/particle is included in the statistical information ultimately provided to the user.

For any spot that is not within pre-set parameters, the software further analyzes the spot to determine how many separate circular bubbles form the spot. If the number is less then a pre-set number of bubbles, the ratio of the area of the spot versus the sum of the areas of the circular bubbles forming the spot are calculated. If this calculation is less then a pre-set threshold value, the user can choose whether or not to include this information in the above referenced statistical data provided to the user.

This above referenced information can be provided as numerical data in a report as well as displayed visually on a monitor 78. For example, spots appearing as single round bubbles of a desired size can be shown in green whereas spots formed by multiple bubbles that meet the above referenced criteria can be shown in yellow. Spots that were filtered out of the data based on the above calculations can be shown in red, and spots touching the border or invalid (ie., cling-on) bubbles/particles can be shown in black.

Accordingly, the user can ascertain the size, volume, quantity and other characteristics of the bubbles/particles being injected into the process liquid in a vessel in real-time. Various adjustments can thereafter be made to process parameters to ensure that the process proceeds in a desired manner.

The above referenced calculations by the software provide only one contemplated example. The software can be designed to determine other information. For instance, the user may be interested in platelet or rod-shaped particles and not round bubbles. The software can be designed to recognize other shapes and characteristics requested by the user.

While preferred vision analysis systems and methods and preferred image recognition software have been described in detail, various modifications, alterations, and changes may be made without departing from the spirit and scope of the present invention as defined in the appended claims.

The invention claimed is:

1. A method of analyzing bubbles, cells or other particles in a process liquid contained in a vessel, comprising the steps of:
   obtaining images of the bubbles, cells or other particles in the liquid in-situ with a vision probe extending into the vessel;
   generating a binary image for each image, each binary image having a background with spots located thereon corresponding to the bubbles, cells or particles appearing in the images;
   analyzing the binary images with image recognition software to determine information concerning a process occurring within the vessel; and
   adjusting a process condition of the process occurring within the vessel based on the information determined from said analyzing step;
   said analyzing step including measuring at least one of bubble, cell or particle size, mean diameter, surface area, flow rate, flow pattern, population distribution, viability, agglomerates or clumping, color change, viscosity, Sauter mean, ratio of surface area of bubbles relative to volume of bubbles, gas hold-up ratio of gas volume to volume of liquid, and interfacial area;
   said analyzing step including identifying valid or viable bubbles, cells or particles from invalid or non-viable bubbles, cells, or other particles appearing in the images by distinguishing the invalid bubbles, cells or particles that appear in the images and that are stuck to the vision probe relative to the valid bubbles, cells or particles that are freely flowing in the process liquid; and
   said distinguishing step being accomplished by determining which bubbles, cells or particles appear in the same location in each of the images.

2. A method according to claim 1, wherein said images include at least about 100 frames of images.

3. A method according to claim 1, wherein the spots that appear in the binary images that are of a size less than a pre-determined number of pixels are deleted from the binary images.

4. A method according to claim 3, wherein binary images having annular or unfilled spots are filled in such that the spots in the binary images are solid.

5. A method according to claim 3, wherein any spots in the binary images contacting a border of the images are identified as invalid bubbles, cells or particles.

6. A method according to claim 5, wherein data including the location, size and shape of each spot corresponding to one of the valid bubbles, cells or particles is generated.

7. A method according to claim 6, wherein a report presenting the data is generated relative to the data corresponding to spots of a pre-determined shape and size.

8. A method of analyzing bubbles in a process liquid contained in a vessel, comprising the steps of:

releasing gas in the form of bubbles from a sparger in the process liquid within the vessel;

agitating the process liquid with an agitator within the vessel;

obtaining images of the bubbles in the process liquid in-situ with a vision probe extending into the vessel, the images being obtained by projecting light from the vision probe into the vessel to illuminate the gas bubbles and recording the images of illuminated bubbles with a camera mounted on the vision probe, the step of projecting light including emitting or reflecting light directionally from behind the gas bubbles relative to the camera to produce back lit images;

generating a binary image for each of the images, each binary image having a background with spots located thereon corresponding to the bubbles appearing in the image; and analyzing the binary images with image recognition software;

said analyzing step including identifying valid or viable bubbles from invalid or non-viable bubbles appearing in the images;

said identifying of valid or viable bubbles including distinguishing the invalid bubbles that appear in the images and that are stuck to the vision probe relative to the valid bubbles that are freely flowing in the process liquid, the invalid bubbles being distinguished from the valid bubbles by determining which bubbles appear in the same location in each of the binary images; and said analyzing step including measuring bubble size, mean diameter, surface area, flow rate, flow pattern, population distribution, viscosity, Sauter mean, ratio of surface area of bubbles relative to volume of bubbles, gas hold-up ratio of gas volume to volume of liquid, and interfacial area.

9. A method according to claim 8, wherein said analyzing step is performed in substantially real time, and further comprising the step of controlling a process condition in the vessel based on said analyzing step.

10. A method according to claim 9, wherein said step of controlling includes adjusting a flow rate of gas through the sparger, adjusting a rate of rotation of the agitator, adjusting temperature, or adjusting turbidity.

11. A method according to claim 8, wherein said step of obtaining images only occurs at preset intervals of time, and wherein light is only projected from the vision probe during the pre-set intervals.

12. A method according to claim 8, wherein the vision probe is flexible, and further comprising the step of re-positioning the vision probe within the vessel during an on-going process to observe a different region of the process fluid within the vessel, wherein said step of re-positioning the vision probe includes articulating the probe via a ball joint.

* * * * *